United States Patent [19]

Silverschotz et al.

[11] Patent Number: 5,087,805
[45] Date of Patent: Feb. 11, 1992

[54] PRINTED AND ENCODED MASS DISTRIBUTABLE RESPONSE PIECE AND METHOD OF MAKING THE SAME

[75] Inventors: Stanford Silverschotz, Livingston; George P. Hipko, Milltown, both of N.J.; Michael Dennis, Doylestown, Pa.

[73] Assignee: Webcraft Technologies, Inc., North Brunswick, N.J.

[21] Appl. No.: 430,869

[22] Filed: Oct. 31, 1989

Related U.S. Application Data

[63] Continuation-in-part of Ser. No. 360,040, Jun. 1, 1989, Pat. No. 4,939,888.

[51] Int. Cl.$^5$ .............................................. B23K 26/00
[52] U.S. Cl. ............................. 219/121.71; 219/121.7; 219/121.82
[58] Field of Search ............. 219/121.7, 121.71, 121.6, 219/121.85, 121.82; 346/76 L; 235/375, 385

[56] References Cited

U.S. PATENT DOCUMENTS

| | | | |
|---|---|---|---|
| 4,316,073 | 2/1982 | Lemelson | 210/121.71 |
| 4,523,777 | 6/1985 | Holbein | 346/76 L |
| 4,675,498 | 6/1987 | Lemelson | 219/121.62 |
| 4,692,394 | 9/1987 | Drexler | 346/76 L X |
| 4,711,996 | 12/1987 | Drexler | 346/76 L X |
| 4,774,522 | 9/1988 | Van Tongeren | 346/76 L X |
| 4,939,888 | 7/1990 | Katz et al. | 53/411 |

Primary Examiner—C. L. Albritton
Attorney, Agent, or Firm—Shlesinger Arkwright & Garvey

[57] ABSTRACT

A method of simultaneously encoding successive groups of printed paper sheets or mass distributable material wherein the sheets are provided with unperceptable and virtually invisible common code pattern by laser means which is supplied with a distinct series of coded pulse signals in synchronism with control pulses to produce a different optically-scannable coded hole pattern on each group of printed sheets.

20 Claims, 5 Drawing Sheets

PRINTED AND ENCODED MASS DISTRIBUTABLE RESPONSE PIECE AND METHOD OF MAKING THE SAME

This application is a continuation-in-part of U.S. Pat. application Ser. No. 360,040, filed June 1, 1989 and subsequently issued as U.S. Pat. No. 4,939,888 on July 10, 1990.

FIELD OF THE INVENTION

This invention relates to mass distributed response items, and more particularly to such an item and method of making the same in which the recipient of a mass distributed response piece, such as a coupon or order form permits the recipient to be readily identified.

BACKGROUND OF THE INVENTION

In the advertising business, it is a current practice to target individuals and groups of individuals for specific advertisements. It is important in the advertising business to know something about the individual to whom the advertisements are being sent. Demographic information is commonly used to target groups or individuals by focusing on common characteristics. Characteristics which are generally focused on include geographical areas, income, gender and age, current purchasing patterns and habits, etc.

While the name and address of the individual to whom the advertisement is being sent is usually known, it has been heretofore difficult to determine which individuals have responded to the advertisements, such as one who redeems a coupon to make a purchase.

Coupons, as currently printed, may include a bar code or some other coding identifying the product, and possibly the sales campaigns. But it has not been practical because of the space required by bar codes or other optically readable coding to print a separate code on each coupon identifying the individual household or addressee to which the advertisement and coupon is sent.

Those knowledgeable in this field will appreciate that there is a need for a service or merchandise coupon advertisement coding system which allows advertisers to uniquely identify those individual customers who respond to their advertisements.

In addition, in many instances it is impractical to place a code on coupon pieces, where for example, many and/or different multiple advertising pieces are contained in a common packet to be sent to an individual addressee, or where the advertising and coupon pieces are signature inserts in a publication to be forwarded to a particular addressee or household.

FEATURES AND SUMMARY OF THE INVENTION

Accordingly, a feature of the invention is the providing of a unique coding method for a mass distributable response piece without being restricted by space availability or printed material on the sheets.

Another feature of the invention is to provide a method capability of simultaneously encoding all of the paper sheets in the stack simultaneously with a common code marking, irrespective of the number of sheets in that stack or group.

Yet another feature of the invention is to provide a method in which all of the printed paper response sheets in a stack are encoded simultaneously with a common code pattern to identify the individual or addressee who is to receive that group of response pieces.

A further feature of the invention is to provide a method in which successive groups of printed paper sheets are quickly and successively moved passed the apparatus which applies a different code to each stack.

Yet another feature of the invention is to provide a mailing piece formed of a plurality of sheets gathered together in a group or stack, where each of the mailing pieces has the same code and which is formed by a spaced linear series of perforations therein forming a distinctive code pattern.

Yet another feature of the invention is to provide a coding method that can be placed anywhere on the printed sheet without interfering with the printed graphic material on the sheets and is unperceptable and virtually invisible to the reader.

Another feature of this invention is the simultaneous encoding of a group of previously gathered printed paper response sheets by making a common series of holes through each sheet in the group, the holes being of such a size that they are unperceptable to the casual viewer, but can be scanned by optical equipment.

A further feature of this invention is to integrate the encoding of the printed response pieces as one of the manufacturing steps used to produce the finished packet containing a set of printed response pieces.

These and other features and advantages of the invention will be readily apparent in view of the following description and drawings of the above-identified invention.

DESCRIPTION OF THE DRAWINGS

FIG. 16 is a side view of the separating assembly of FIG. 9.

DESCRIPTION OF THE INVENTION

Figures 1, 2, 3:
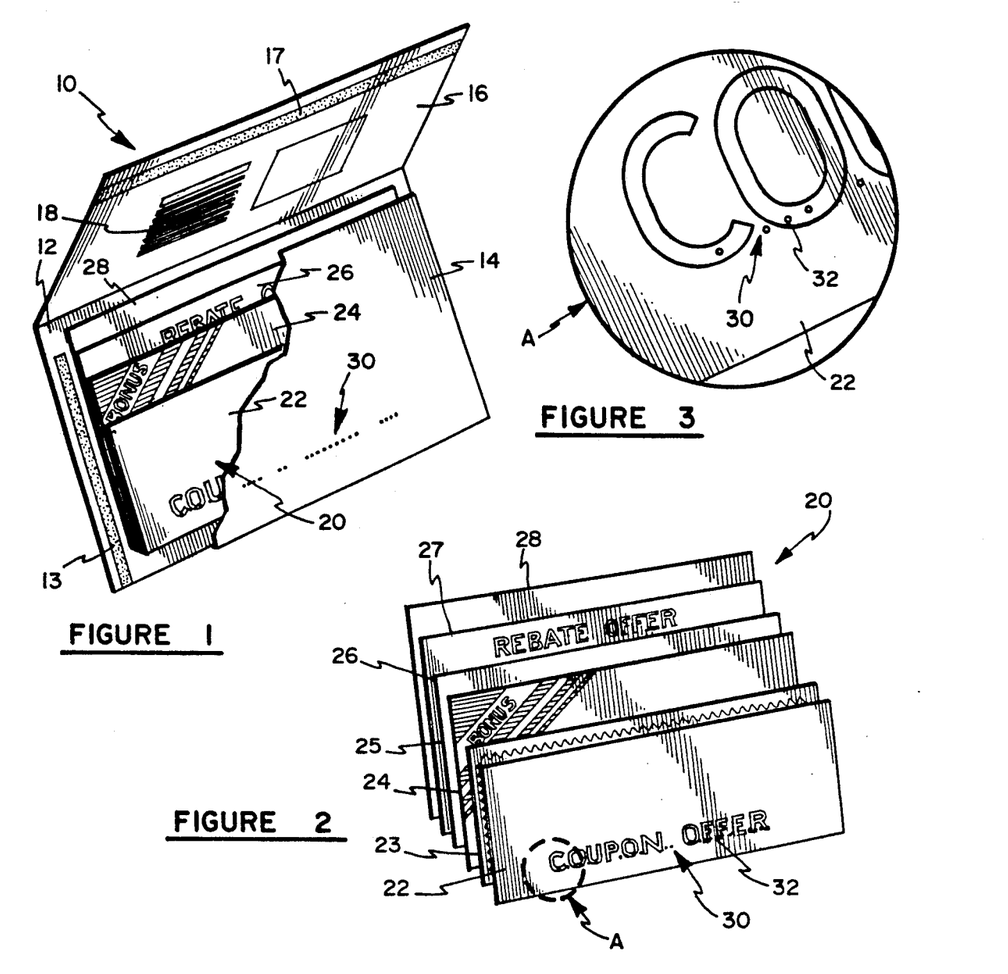
FIG. 1 is a perspective partial cut-away view of an envelope containing an advertising and coupon packet.
FIG. 2 is a perspective view of the packet items contained in the envelope of FIG. 1.
FIG. 3 is an enlarged plan view of a small part of the area of the upper coupon of FIG. 2 which contains some code holes.

An advertising mail-out packet typical of this invention is shown in FIGS. 1 and 2. An outer envelope generally indicated at 10 contains a number of advertising pieces generally indicated at 20 which are encoded by a single common hole pattern generally indicated at 30. The envelope 10 is an in-line produced type which has a rear address panel 12 and an upper pocket panel 14 held together along their common side edge by a glue strip 13. The envelope flap 16 is relatively wide and contains advertising material 18 and a closure glue strip 17. The set of advertising inserts 20, as shown in FIG. 2, includes individual coupons 22 and 23, a fold over insert having sheets 24 and 25 and a double fold piece having panels 26, 27, and 28. A single line of small visually unnoticeable holes or perforations 30 marks each of the sheets of packet 20 with a common machine readable coded pattern which identifies the addressee. The perforations are shown in the drawings for the purpose of clarity to be larger than they would appear in the actual mailing packet. The coded hole pattern is produced by an intermittently controlled pulse operated industrial laser beam which passes through the entire envelope 10 and its contents.

The enlarged section, generally indicated at A of coupon 22 of FIG. 2 is shown in FIG. 3. Note the relatively small size of the holes with respect to the printing. The holes 30 are typically seven thousandths of an inch in diameter. The small size permits the coded line of holes to be applied anywhere on a sheet without visually interfering with the printed message. Consequently, the hole pattern can simultaneously be made on a large number of differently printed pieces with no constraint as to where the code may be placed. Furthermore, the code may be placed in a book or magazine. This allows for coding of inserts in a book or magazine after binding with no interference with the readability of the printed articles or aesthetic qualities of photographs. In this respect, a hole or perforation size of 7 mils diameter would ordinarily be visually unnoticeable. In most situations, a hole size of 5 mils or less cannot be seen by the unaided human eye. It is possible to optically scan hole sizes in this range or even smaller, with optical scanning devices which are part of high speed machine readable systems.

Figure 4:
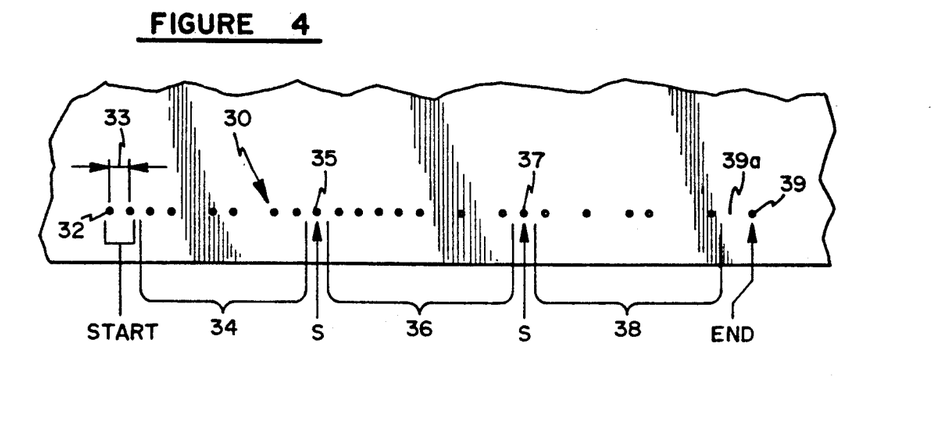
FIG. 4 is an enlarged plan view of the surface of the envelope of FIG. 1 containing a typical hole code.

The preferred hole code arrangement is a binary pattern, as illustrated in FIG. 4. In these systems, a light source is usually placed behind the coded sheet, and a photocell on the other side senses the light which passes through the holes. The first two holes 32 are a start signal or preamble for the electro-optical reader. By changing these parameters, this distance can be either reduced or lengthened. As an example, a ⅛th inch spacing center to center between hole positions for a piece traveling at 250 feet per minute under a laser beam having a frequency of 400 pulses per second. The length of the code on the coupon for a 32 bit binary code would be four inches. Each of these parameters, however can be varied. However, the laser may be pulsed at 1000 pulses per second or even faster. At the increased pulse rate, the web speed may be increased, or the code may be repeated to provide greater reliability. For example, the pulse rate is increased to 800 pulses per second, the code can be repeated a second time in the same code length, so that the reliability of the reading may be increased by requiring the optical reader equipment to obtain a second matched reading. There is a great deal of flexibility in this respect, since the holes can be read at much closer spacing, and the pulse rate may be increased to as much as 2500 pulses per second. This will readily accommodate bindery applications where the pieces are moved at approximately 500 feet per minute.

Following the preamble of the code, is first code section 34 consisting of ten spaced potential hole positions followed by a synchronizing pulse position 35. The synchronizing pulse position 35 will always be made by the laser. The optical machine reader will sense the presence or absence of this hole to assure that the code has been correctly applied to the piece. There are ten code positions in the first code section 34. The intermediate section 36 and synchronizing hole position 37 are a repeat of the first code section arrangement. The final code section 38, is a twelve position potential hole stage followed by two synchronizing or end pulse hole position. However, only the last hole 39 is made. The hole position 39a is never made, while the hole 39 is always made for each code. The code arrangement will be discussed in further detail with respect to FIG. 13.

The total number of potential code hole locations is 32. Each location represents a binary code digit. For example, a hole represents a zero and the absence of a hole represents 1. This will correspond with multiple 32 position reader equipment.

A code arrangement with this number of combinations is useful for a mass mailing of coupons and advertising solicitations, where each single code combination identifies a particular addressee to whom the letter is addressed. In the case of a coupon which is encoded, the advertiser has the ability to determine which addressee or recipient has redeemed the coupon. The sectional code arrangement makes it possible to also add further identifying information, either with respect to the addressee or the advertiser and product, all of which could provide rapid machine sorting of large numbers of redeemed coupons.

Figure 5:
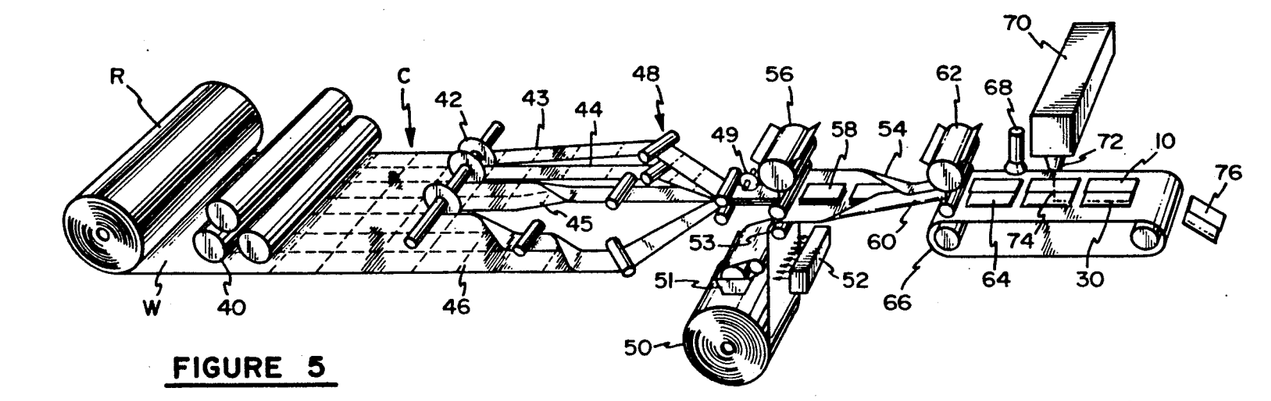
FIG. 5 is a perspective schematic view showing a method of manufacturing the advertising packets containing envelope of FIG. 1.

An in-line method producing the advertising envelope packet of FIG. 1 is illustrated in FIG. 5. Roll of paper R supplies a web W which produces the entire packet insert pieces. As shown in FIG. 5, the web passes through a multi-color press generally indicated by printing rolls 40 which print the insert sheets of advertising insert 20. The web W then passes under a ribbon cutter assembly 42 which slits the web into ribbons 43 and 44 containing coupons 22 and respectively. The other larger ribbons 45 and 46, which are subsequently folded as generally indicated, contain the remaining sheets of the packet. Ribbon 45 is folded over edge to edge and contains the intermediate sized advertising and coupon pieces 24 and 25. These pieces contain advertising as well as coupon sections, not shown in FIG. 2. Ribbon 45 is edge folded to position the section containing the series of advertising pieces 24 over the series of advertising pieces 25.

It should be noted that the web W is printed with the insert pieces positioned lengthwise in transverse side by side sections containing the series of repeated prints of strips which are aligned with the roller cutters of the cutter assembly 42. Each set of inserts 58 for a single packet are transversely aligned with each other across the web. This arrangement is generally indicated in the web section C.

Ribbon 45 is folded along the common line forming the edge of the two adjustment strips containing advertising pieces 24 and 25. In similar fashion, web 46 is successively folded along the common lines between the three printed strips containing advertising pieces 26, 27, and 28. The turn bar assembly generally indicated at 48 positions the respective ribbons into superposed relationship in the order in which they will appear in the packet. The superposed ribbons are then passed through an edge slitter 49 which removes longitudinal fold line joining sheets 24 and 25, and 26 and 28.

The roll of web 50 supplies the envelope wrap. It passes under the addressing imaging bar 52 of a dot matrix printer such as a Mead or Diconix ink jet imager, which places the successive addresses on each successive envelope address panel, corresponding to the rear envelope panel 12 of FIG. 1. The continuous web passes over the roller 53 and into a horizontal position providing a receiving section 54 beyond and below the transverse cutter assembly 56. The superposed ribbons 49 are cut transversely along the common transverse line separating successive advertising pieces in the respective ribbons by cutter 56.

Each of the severed advertising piece sets 58 is the advertising insert pack 20 of FIG. 1. Each set 58 drops onto the web receiving section between previously applied transversely extending glue lines (not shown) which are the envelope glue lines 13 of envelope 10 in FIG. 1. The closed envelope is then formed by folding the inner pocket panel section 14 over the inserts and subsequently folding the envelope flap 16 for the pocket panel. The folded envelope wrap 60 then passes through the cutter assembly 62, which transversely severs the successive and completed envelope pieces 64. The advertising envelope pieces 64 fall onto conveyor 66. The photocell sensing assembly 68 senses the edge of the oncoming envelope detector for the industrial laser 70. An appropriate delay, depending upon the speed of the envelope piece controls the laser output from the laser 72 which produces a cutting beam 74 to make the successive hole pattern code 30 on the envelope packet 10. This hole code pattern is different from the code on the previously encoded piece 76 which falls from the conveyor. The encoded hole pattern corresponds to the addressee whose name and address has been placed on the envelope by imaging bar 52 as it left the glue stage 51.

Figure 6:
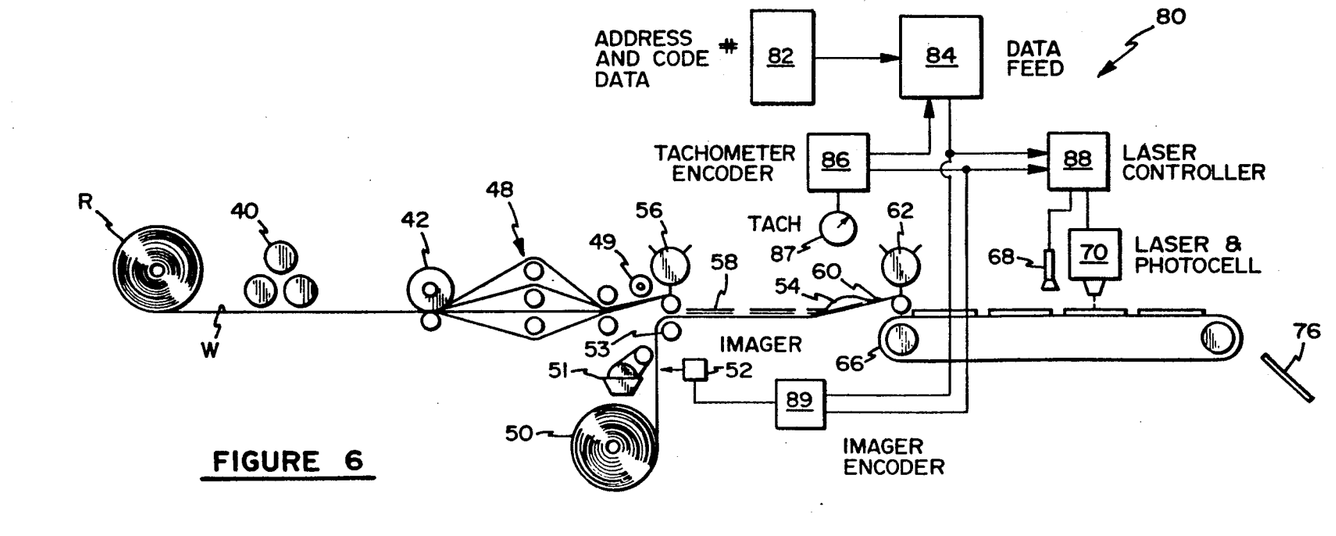
FIG. 6 is a schematic view of the method of producing the packet of FIG. 1, illustrating the control functions for the encoding and address operations.

The manner of controlling the application of the imaging of the addresses and the encoding of the hole pattern on the finished piece is shown in FIG. 6.

This is a schematic side view of the production assembly of FIG. 5 showing the control system generally indicated at 80 for supplying the appropriate address and code information to the ink jet imager bar 52 of a dot matrix printer and the laser 70. The address and code number data is contained in an appropriate storage data device 82, such as a magnetic tape, or disk, the output of which is supplied to a data feed control 84 which is a microprocessor. The data feed control 84 correlates the address and its corresponding code so that both control data are entered on the same finished piece.

The timing control pulses are supplied by the tachometer encoder unit 86. The tachometer 87 connected to the conveyor 66, the speed of which is synchronized with that of envelope web from paper roll 50. A clock or control pulse which is a function of the speed of the conveyor and wrap web is supplied to the data feed processor 84, as well as to the laser controller circuit 88, and the imager control circuit 89. The data feed processor 84 is also connected to both controllers 88 and 89. Operation of the imager 52 is set to successively image the address panels 12 of the envelopes with different successive addresses of recipients. The envelope production includes conventional printing and glue application stages, not shown. The operation of the imager 52 is programmed in the imager control circuit 89 to apply address data on envelope blank address panels of the web at regular spaced intervals depending upon the web sped pulse received from the tachometer encoder.

The operation of the laser 70 is similarly controlled by the laser controller 88. However, the operation of the laser 70 is synchronized with the movement of the completed and separated advertising packet 64. The photocell 68 senses the leading edge of the packet, and sends an impulse to the laser controller 88. This signal initiates a delay train of the predetermined number of pulses before which the laser will operate. This permits the packet 64 to travel into position below the laser 70 for receiving the coded laser beam signal 74. Typically, the speed of travel of this in-line process is 250 feet per minutes. The tachometer encoder permits a control or clock pulse train of 400 pulses per second. This pulse train ensures that the laser holes will be placed on the spaced hole pattern where successive pulses are spaced $\frac{1}{8}$th of an inch apart. In a bindery, the web speed can be from 450 to 500 feet per minute. Consequently, if a desired hole spacing were to be obtained, the laser pulse rate would be varied.

In the preferred embodiment, the laser assembly 70 is a water cooled industrial type carbon dioxide laser which is designed for enhanced pulsing. A laser of this type is the EVERLASE trademark S-48 unit manufactured by Coherent General. This model of laser would have a typical power range of 300–950 watts and a typical peak power of 5400 watts. The laser beam width can be varied by adjustment of a focus control 72. The preferred laser produced hole is 7 thousandths of an inch in width.

The code output of laser 70 is produced by the laser controller 88 which superimposes the code data from the data feed processor 84 onto the block pulse train received from the tachometer encoder 86. The laser will operate at a frequency matching the 400 cycle per second frequency of the tachometer encoder control pulse train.

Figures 7, 8A, 8B, 9:
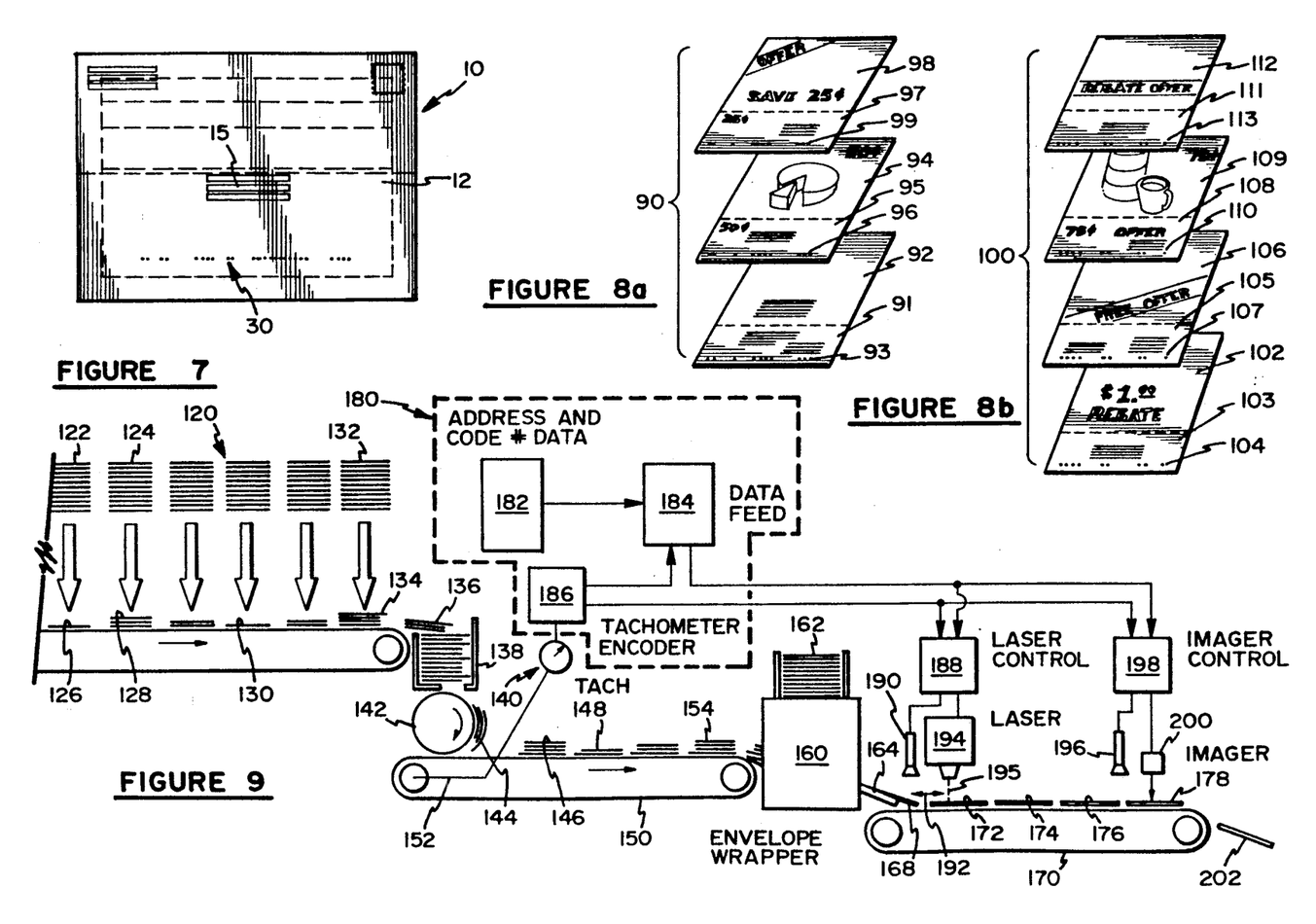
FIG. 7 is a plan view of the address face of the advertising packet of FIG. 1.
FIG. 8a is a perspective exploded view of an assembled set of different advertising pieces encoded with the same hole code.
FIG. 8b is an exploded perspective view of different advertising pieces having the same hole code.
FIG. 9 is a schematic view illustrating the method of producing and encoding successive packets containing different groups of printed sheets or inserts which differ in both quantity and type, such as shown in FIGS. 8a and 8b.

FIG. 7 shows the outer address face or address panel 12 of the envelope 10 of FIG. 1. The imaged address of the recipient 15 matches the hole code 30 of that individual. This information is supplied from the address and data code number generator 82 of FIG. 6. The master listing of names and addresses with corresponding codes for each is contained in the address and code number data unit 82, for an entire mailing. Subsequently returned coupons having the hole code can be read mechanically and correlated with the name and address of the recipient to whom it was originally mailed.

The advertising packet of FIG. 1 is restricted to identical insert content for each addressee. However, it is also possible to vary the content of successive packets according to the particular addressee. FIGS. 8a, 8b and 9 refer to such variable content advertising packets and the method of producing them.

The groups of advertising pieces of FIG. 8a have the same general format, but are each different. They can be either from a common advertiser, or different advertisers in a cooperative or syndicated mailing. The lowermost coupon 91 is part of a single sheet insert having an upper advertising section 92. The coupon has a binary coded hole pattern 93 of the same type of the binary coded hole pattern 30 of FIG. 7. The intermediate advertising insert is similarly arranged with an upper advertising section 94 and the lower coupon section 95 containing the hole pattern 96. Different coupon and advertising pieces having an upper coupon section 98 and a lower coupon section 97 with a binary, linear, laser-produced coded hole 99 is also included as part of this three piece advertising insert set. Although the format is the same, with the coupon at the bottom of the advertising piece, the printed material on each of the advertising pieces is different. Obviously, the number and content of the pieces can be varied. The laser assembly 70 is capable of cutting holes through 25 or more typically 0.0035 inches thick paper sheets simultaneously. Each of these different printed pieces would receive the same coded hole marking.

FIG. 8b shows a second group of advertising pieces in superposed relationship which comprise one common insert for an envelope. The format of the advertising piece with a lower detachable coupon section is similar to the format of the advertising inserts of FIG. 8a. There are four advertising inserts in this group 100, constituting coupons 103, 105, 108 and 111. Each has a corresponding upper advertising section, 102, 106, 109, and 112, respectively. All of the coded hole patterns on the coupons, 104, 107, 110, and 113 are identical and identify the intended recipient or addressee.

The manner of producing such a packet, involves selective feed, and is illustrated in FIG. 9.

The selective feed assembly, generally indicated at 120 has a large number of supply columns generally indicated schematically, such as 122 and 124. It is possible to have as many as one hundred or more such dispensers feeding onto a common conveyor, each section of which would be designated to receive advertising pieces for a particular addressee. For example, dispensing column 122 could contain advertising insert 98 of FIG. 8a and dispensing column 124 would contain only the inserts 110 of FIG. 8b. These inserts would be selectively released by appropriate control means to supply a single advertising insert, from the column 122 onto the piece 126, for example. Similarly, the advertising piece in column 124 would be deposited as the top sheet on the group of inserts 128 carried by the conveyor. Each of the successive groups of inserts receives a designated addition as it passes under the successive feed station positions.

Figure 14:
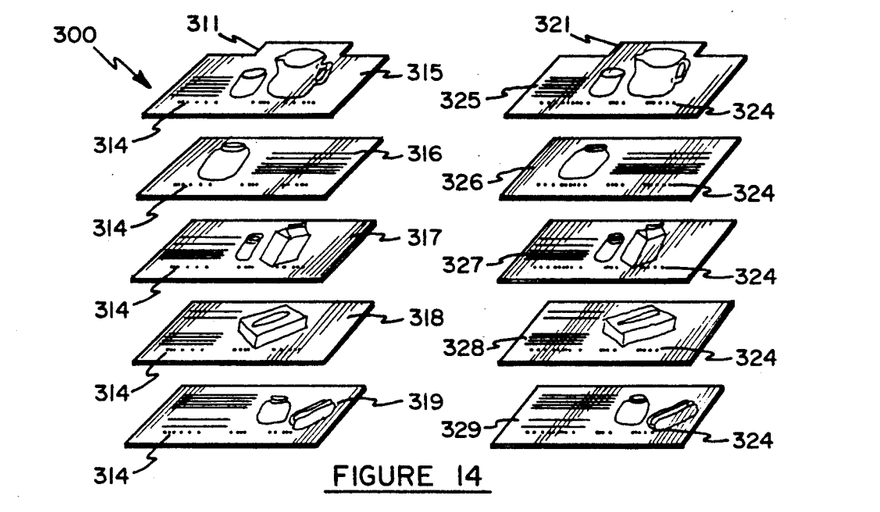
FIG. 14 is an exploded view of two groups or stacks of printed pieces.
Figure 15:
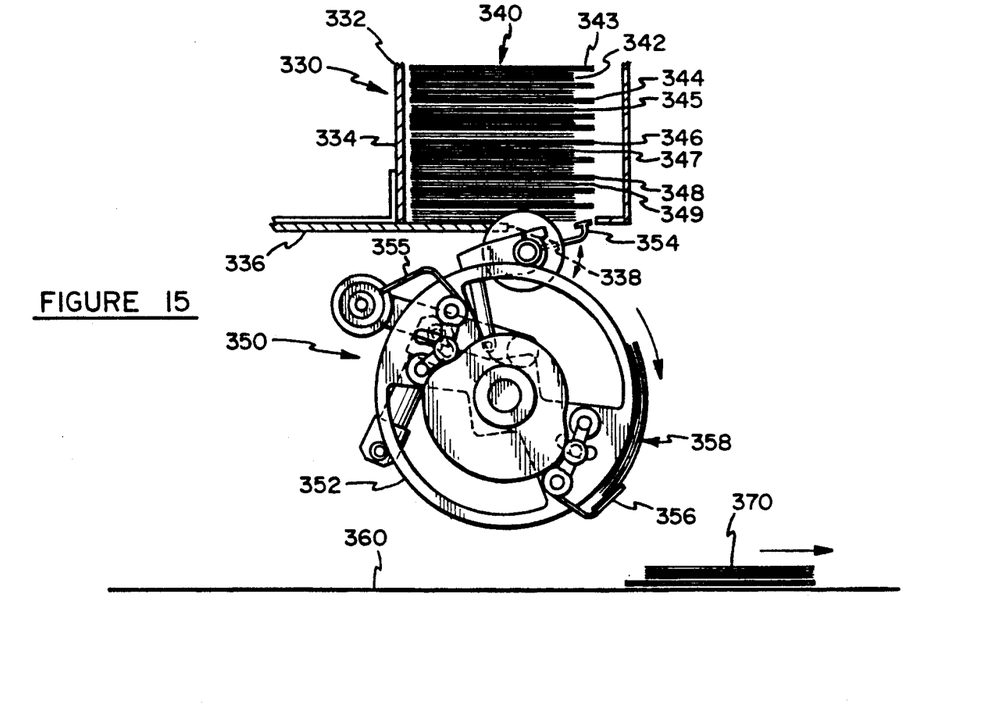

Column 132 contains a piece which has a separator tab 134. Every pile receives sheet 134 which has a separator tab. FIGS. 14 and 15 illustrate in further detail the tab containing piece, and the hopper and sheet feeder assembly 142.

When a completed set of advertising pieces 136 leaves the conveyor, it can be wrapped as shown in FIGS. 5 and 6 or it can be fed directly to an envelope wrapper assembly such as 160 in FIG. 9. In those instances where the traveling speed of the conveyor 130 varies somewhat from the output rate of the envelope wrapper 160, it may be desirable to add a separator sheet or separator tab to the top of the group of advertising inserts 136, and to each group of advertising inserts when it reaches this point. The advertising insert groups are then fed to the hopper 138. The sets of advertising pieces are successively removed from the bottom of the hopper 138 by a sheet feeder assembly 142 which is slightly modified to successively remove the lowermost group or set of coupon piece from the hopper. The separator sheet tab or extended section is grasped and pulled together with the entire set from the bottom of the hopper to rotate it downwardly as shown at 144 where it is placed immediately behind the previously selected groups of advertising inserts 146 and 148 on conveyor 150. The speed of the conveyor is measured by the tachometer assembly 140 which is electrically connected to a tachometer generator not shown through line 152. Conveyor 150 carries groups of advertising inserts as indicated 154, where the inserts are loaded into the envelope wrapper 160. Pre-printed envelopes 162 are contained in the loading hopper at the top of the envelope wrapper unit. The completed assembly leaves the wrapper by a guide 164 and moves into contact at 168 with the processing conveyor unit 170. The speeds of conveyors 150 and 170 are synchronized to provide an even flow of insert sets and filled envelopes through the assembly.

The conveyor 170 carries a packet 172 beneath the laser where it is encoded by the laser. Encoded envelopes 174 and 176 are then moved into position 178 beneath the imager where an address is applied. The address and coding information, as well as timing control with the movement of the conveyors 150 and 170 is supplied by the address and data section 180.

The control for the imager and the laser are similar to the control units previously described with respect to FIG. 6. Address and control number data block 182 supplies each of the addresses for the envelopes with the corresponding control number for the addressee. In this instance, although not shown, processing of this data is also coordinated with each of the advertising packets assembled on conveyor 130. In this production line, it is necessary to keep track of each advertising packet made up for a particular addressee, such that after it is wrapped, the correct code number and address is applied to the envelope. Since there is a continuous production process, effective timing control and appropriate delay intervals are used to apply the correct information to a given packet, such as 172 as it passes beneath the laser encoding station. Tachometer 140 receives an electrical signal from a transducer along line 152, which is supplied to the tachometer encoder 186. The tachometer encoder produces the series of clock pulses which indicate the speed of the conveyor 150 (synchronized with conveyor 170) to control operation of the laser control unit 188 and the timed feed of address and code number data to the laser pulse control circuit. The photocell 190 senses the edge of envelope 168 and provides the appropriate time delay to permit travel of the envelope to the encoding position under the laser 194, where the pulsed beam 195 produces the coded sequence for that envelope. Appropriate additional delay is built into the control system such that the imager control circuit 198 controls application of imaged printing through the imager (dot matrix printer) ink jet control bar 200. Precise sensing and timing is provided by the photocell pick-up 196 which measures the edge of the approaching envelope packets.

It should be noted that there is some complexity in applying the control data applied by the laser 194 to a given envelope such as 172 which is different from the address information being applied by the jet image control bar 200 at that moment. In this assembly, the imager is applying an address to an envelope corresponding to a coded hole sequence applied previously. In this instance, assuming a long address list, the laser is applying a control code for a name on the list three names earlier than the addressee being imaged on the envelopes. The completed packet 202 containing both the coded hole, and the address, is complete and ready for mailing.

Figure 10:
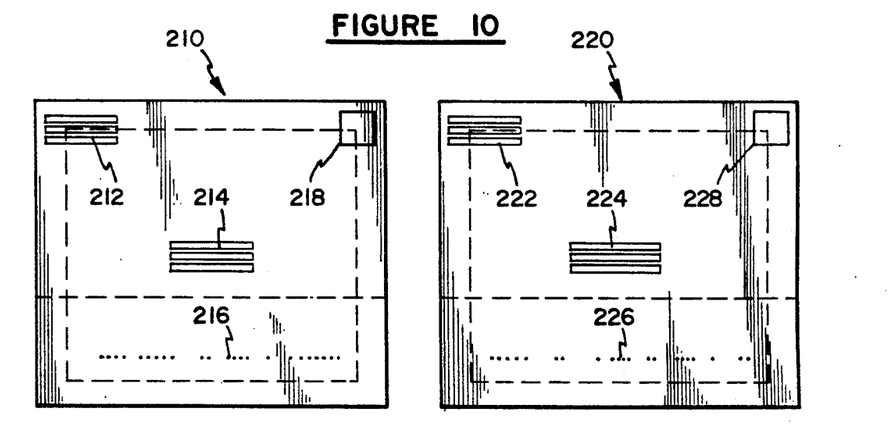
FIG. 10 is a plan view of two successively produced packets assembled by the apparatus of FIG. 9.

FIG. 10 shows a completed advertising packet 210 with a return address 212, the ink jet imaged address 214 of the addressee, the coded hole pattern 216 made by the laser, and the stamp section 218, after completion of the ink jet imager by the imager bar 200 of FIG. 9. A second advertising mail-out packet 220, similar to packet 210, also produced by the method of FIG. 9, has pre-printed return address 222 and stamp sections 228. The ink jet imaged address 224 could be the next name on the mailing list, where these packets 210 and 220, are successively produced. The encoded laser hole pattern 226 would correspond to the addressee's name and address printed at 224.

Figure 11:
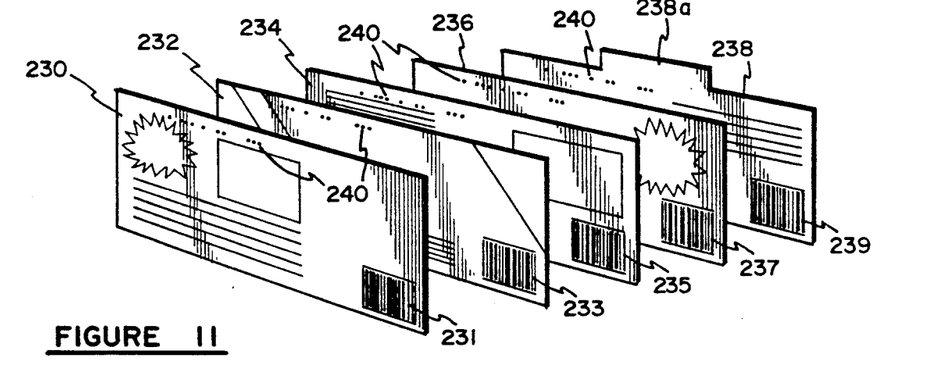
FIG. 11 is an exploded perspective view of a pile of coupons simultaneously logged with a common hole encoded pattern for identification purposes.

The use of a common coded control number for a number of individual pieces for identifying and tracking coupons is illustrated in FIG. 11. A group of redeemed coupons, shown in exploded view for illustration which have been simultaneously marked with a single common laser produced hole pattern, is shown in FIG. 11. Different coupons, 230, 232, 234, 236, and 238 are assembled in a group and passed under a code controlled laser which applies simultaneously a single coded hole pattern 240 to all coupons. Note that coupon 238 has a tab 238a. This piece corresponds to the tab piece 134 which was the last and top piece applied to the successive piles in the manufacturing method illustrated in FIG. 9.

Coupons can be from different manufacturers representing different products and prizes, and are machine readable by the bar codes 231, 233, 235, 237 and 239 of the coupons. The laser coded pattern permits the machine reading of additional information developed subsequent to the distribution of the coupons themselves or sorting purposes, such as identification of the store or area where the coupons were redeemed, etc. This application is distinct from the application of FIG. 8 in which the coded hole pattern identified the single addressee, or possibly other data known before distribution of the advertising pieces.

Figure 12:
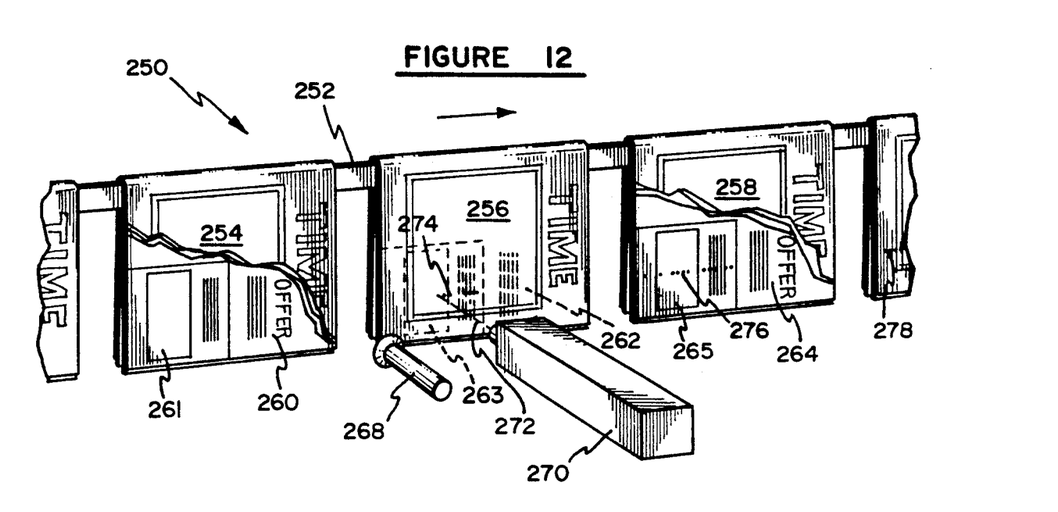
FIG. 12 is a perspective view showing the laser encoding creating a code by applying a coded series of holes on each of the successive multi-page signatures on a line conveyor.

The application of a common laser produced hole code for coupons or other markings, which can be placed over pre-printed material without visually disturbing effect, or without requiring exclusively designated area for the code, is a particular advantage that can be used for both individual advertising pieces, or those to be bound in a magazine or booklet. The use of a laser for the signatures of a booklet or bound piece is illustrated in FIG. 12 by the assembly generally indicated at 250. A conveyor 252 carries a succession of multiple signature pieces 254, 256 and 258. These are magazine signatures containing a internal advertising and coupon offer 260, part of which is a coupon 261 which is to be tracked by encoding, as shown in the cut-away section of the signature 254.

The intermediate signature 256 shows in dotted outline the internal advertising piece 262 and its corresponding coupon section 263 which is to be marked. The photodetector, generally indicated at 268 is used to sense the leading edge of a signature. It acts in the same fashion as the photodetector 190 of FIG. 9. Laser 270 is shown in the process of applying a pulsed code output 272 to the coupon 263. Previous holes 274 of the code to be applied are shown. Note that they pass through all of the pages of the entire signature, including the advertising page. In this respect, it is possible to encode internal pieces. Since the code holes are below ordinary visual perception levels, all pieces of the signature can be penetrated by the laser without visually marring any of the pages in the signature group.

The cut-away signature group 258 discloses the advertisement page 264 with the code 276 on the coupon 265. The codes 274, 276 and 278 will each be different and will correspond to a designated addressee or household.

The photo detector generally indicated at 268 indicates the leading edge of an approaching signature 254, and will control initiation of a fixed time interval delay after which the laser 270 will begin placing the hole pattern presenting the control number for the signature 254. The ability to place an unobtrusive and visually non-perceivable marking over pre-printed material at any location provides additional flexibility in a bound item, since the code can be applied to many pieces simultaneously, many of which are not designated to receive a code.

Figure 13:
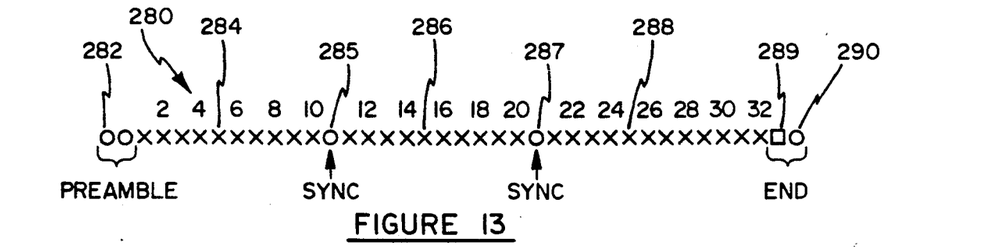
FIG. 13 is a layout of the binary code arrangement used for encoding.

The details of the code are shown in FIG. 13. The code generally indicated at 280 illustrates a 32 hole position code arrangement. It has a preamble position of two holes 282 and three code hole sections 284, 286 and 288. The hole positions for the code are placed on the designated hole position grid which is shown as a line of horizontal "x"'s, 284, 286, and 288. The numbers above the "x"'s are numbered, and show three separate groups of hole code positions. The first two groups 284 and 286 having 10 code hole positions, and the last group 288 having 12 code positions for a total of 32 code hole positions. There are two synchronization holes 285 and 287 which are used to assure that the optical reader is synchronized with the hole code positions as originally placed on the paper sheet by the laser. Note that there are a total of 38 hole positions, including two positions for the preamble, two synchronization positions (hole numbers 11 and 21 designated by 285 and 287) and two end of code positions, 289 and 290. The ending of the code is a two position segment having a blank space 289, and a hole 290. All codes will have an ending of this sequence to advise the optical reader of the end of the code. This arrangement permits the code to be read in either direction, since the preamble and the code ending are distinguishable from one another. The 32 binary code positions permit the use of over four billion distinct code combinations. It is also possible to break up the code segments, where each of the segments may be used for a different purpose, such as addressee in one code section, and product and company designation in another code section.

FIG. 14 is an exploded perspective view of two identical sets or groups of advertising coupon pieces. The set generally indicated at 300 has a common linear code 314 for all of the pieces 315, 316, 317, 318 and 319. This set of inserts can be produced by the assembly shown in FIG. 9, the advertising piece 315 will correspond to tab piece 134. Tab 311 of advertising coupon piece 315 extends over and beyond the periphery of the underlying advertising pieces 316, 317, 318, and 319. Similarly, a different code 324 is commonly applied to all of the pieces of the right hand set of pieces, specifically pieces 325, 326, 327, 328, and 329. Advertising piece 325 has an outwardly extending tab element 321.

FIG. 15 shows in detail an assembly 330 corresponding to hopper 138, and feed assembly 142 of FIG. 9. The lower section of the hopper 332 has a side wall 334 and a lower wall 336 forming a container within which the advertising stacks generally indicated at 340 are contained. The uppermost set of advertising pieces 342 has an outwardly extending tab 343. Note that the number of pieces in each of the sets is not necessarily the same, and that sets 345 and 347, for example, are substantially thicker than set 349. However, each of these sets will have the same separator piece, such as 344, 346, and 348. A sheet separator device generally indicated at 350 separates the bottom set of inserts from the column 340. It has a clockwise rotating surface 352 which is coordinated with a reciprocal mounted sucker rod 354. This sucker rod is a hollow suction tube with a surrounding apertures plate which is pivotally mounted, it successively extends into the openings adjacent the edge 338 of lower plate 336, coming into contact with the tab member at the top of the lowermost set of advertising pieces set and pulls it downwardly. At this point the grasping piece 355 moves into position to hold the set against the surface 352. The grasping finger assembly 356 illustrates the manner in which the set 358 is held into position. This equipment is commercially available.

The conveyor 360 receives the set of inserts upon release, and moves the set such as 370 toward the envelope wrapper, as illustrated in FIG. 9.

With respect to inserts, it should be noted that hole sizes up to 15 mils may be unperceptable when the code overlies a busy or dark printed background, and that all of the individual pieces in a closed envelope can be simultaneously encoded for any desired purpose.

While this invention has been described as having preferred design, it is understood that it is capable of further modification, uses and/or adaptations of the invention following in general the principle of the invention and including such departures from the present disclosure as come within known or customary practice in the art.

What is claimed is:

1. The method of simultaneously encoding a plurality of paper sheets, comprising the steps of:
   a) arranging a plurality of different sheets in successive groups;
   b) passing the successive groups beneath a laser which is capable of piercing the sheets of the group simultaneously producing on each sheet with a series of accurately spaced holes which are visually unnoticeable and in their aggregate form a code; and,
   c) operating the laser to place a different coded series of holes on each successive group as its passes the laser, each coded series of holes being exclusively machine-readable.

2. The method of claim 1, including the step wherein:
   a) encoding is performed by a controlled output laser producing a coded output for each group which is correlated to the particular addressee for that group of sheets.

3. The method of claim 2, wherein:
   a) said group moves relatively with respect to the laser during encoding.

4. The method of claim 3, wherein:
   a) movement of said group is synchronized with respect to the laser to permit the placing of the code at the desired location.

5. The method of claim 4, wherein:
   a) forming a binary code at said series of perforation locations;
   b) forming said binary code by selectively drilling holes at said perforation locations; and,
   c) said binary code being formed by the presence or absence of a hole at each of said perforation locations.

6. The method of claim 5, wherein:
   a) said holes are less than 15 mils in width.

7. The method of claim 6, wherein:
   a) moving said group of sheets along a conveyor during encoding; and,
   b) moving said conveyor at a rate of up to 700 feet per minute.

8. The method of claim 7, wherein:
   a) prior to encoding of said group of sheets, applying a pre-addressed envelope wrapper corresponding to said code pattern.

9. The method of simultaneously encoding successive groups of printed paper sheets, comprising:
   a) providing an industrial laser which emits pulsed beams of coherent light capable of simultaneously perforating all of the printed paper sheets contained in the groups;
   b) moving said groups of printed paper sheets along a linear path;
   c) correlating said pulsed beams with the linear speed of the groups of printed paper sheets by applying a series of laser beam controlled pulses to the laser to enable the laser to produce a visually unnoticeable coded hole pattern over a series of potential perforation locations through all of the paper sheets of a given group; and,
   d) supplying for each group of printed sheets a distinctive series of coded pulse signals to the laser which is synchronized with the laser control pulses to produce a different machine readable coded hole pattern on each group of printed sheets.

10. The method of claim 9, further comprising the step of:
   a) forming said paper sheets from a web of paper.

11. The method of claim 8, further comprising the step of:
   a) printing advertising on said web.

12. The method of claim 11, further comprising the step of:
   a) forming groups of paper sheets from the web.

13. The method of claim 12, further comprising the steps of:
   a) measuring the speed of a conveyor moving said groups of printed paper sheets along a linear path; and,
   b) correlating said pulsed beams of said laser with the linear speed of the groups moving along said conveyor.

14. The method of claim 13, wherein:
   a) said linear speed of the groups of paper sheets is at least 250 feet per minute.

15. The method of encoding a response piece disposed within a multiple page signature, comprising the steps of:

a) inserting the response piece as an individual interior page of a multiple page signature,
b) moving successive signatures past an industrial laser capable of piercing the sheets and the interior response piece with a hole having a diameter sufficiently small to be visually imperceptable,
c) pulsing the laser to produce a series of holes on a response piece which form an optically machine readable code, and varying the code for each group of signatures to provide a different code for each successive coupon piece.

16. The method of encoding a response piece in a signature as set forth in claim 15, including the step of:
a) applying a code to each response piece of a given signature which corresponds to the addressee or recipient of that signature.

17. The method of simultaneously encoding successive groups of paper sheets, comprising the steps of:
a) arranging a plurality of sheets in successive groups along a conveyer;
b) inserting the successive groups into an envelope-wrapper having a distinctive addressee for each successive group of sheets; and,
c) encoding the sheets of each group simultaneously through the wrapper with a coded series of perforations from a laser to identify the addressee.

18. The method of claim 17, including the step of:
a) selectively building each group of sheets to assembly distinct type and number of sheets for each group, which is to be sent to a given addressee which is correlated with a particular code.

19. The method of claim 18, including the step of:
a) providing a preprinted web containing a succession of preprinted sheets for the groups; and,
b) separating the sheets from the web to provide the successive groups of sheets.

20. The method of claim 18, including the step of:
a) providing a series of dispensers, each containing a different set of insert sheets, above a conveyor which are individually activatable to selectively build up groups of sheets which are different from each other.

* * * * *